United States Patent [19]

Swauger

[11] Patent Number: 4,484,913
[45] Date of Patent: Nov. 27, 1984

[54] MEDICAL DEVICE ASSEMBLY HOLDER

[76] Inventor: Donald A. Swauger, 20706 Alaminos Dr., Saugus, Calif. 91350

[21] Appl. No.: 424,002

[22] Filed: Sep. 27, 1982

[51] Int. Cl.³ .............................................. A61M 5/00
[52] U.S. Cl. ............................ 604/179; 128/DIG. 26
[58] Field of Search ............... 604/180, 174, 178, 179; 128/DIG. 26

[56] References Cited

U.S. PATENT DOCUMENTS

| | | | |
|---|---|---|---|
| 3,812,851 | 5/1974 | Rodriguez | 604/179 X |
| 4,027,668 | 6/1977 | Dunn | 604/180 |
| 4,129,128 | 12/1978 | McFarlane | 604/174 X |
| 4,250,880 | 2/1981 | Gordon | 604/180 |
| 4,316,461 | 2/1982 | Marais et al. | 604/179 |

*Primary Examiner*—Stephen C. Pellegrino
*Attorney, Agent, or Firm*—Roger A. Marrs

[57] ABSTRACT

A holder is disclosed herein for releasably retaining a conventional syringe in place on the body of a person undergoing medical treatment which includes a flat base having at least two outwardly extending pairs of support members arranged in fixed, parallel spaced apart relationship on opposite ends of the base. A selected one of the support members is provided with a shaped recess for insertably receiving the syringe in conformed relationship and a snap-lock slot arrangement is formed in the selected support member adjacent the recess for releasably retaining the syringe in place. Retainers are operably carried on the holder base for supporting and retaining the tubing used to introduce fluids to the syringe. Hook and pile fastening arrangements are cooperatively disposed on the base for detachably coupling the holder to a limb or other body part of the person. The term syringe includes needles, gravity flow needles, straight intravenous applicator needles, plunger-type syringes or the like.

1 Claim, 10 Drawing Figures

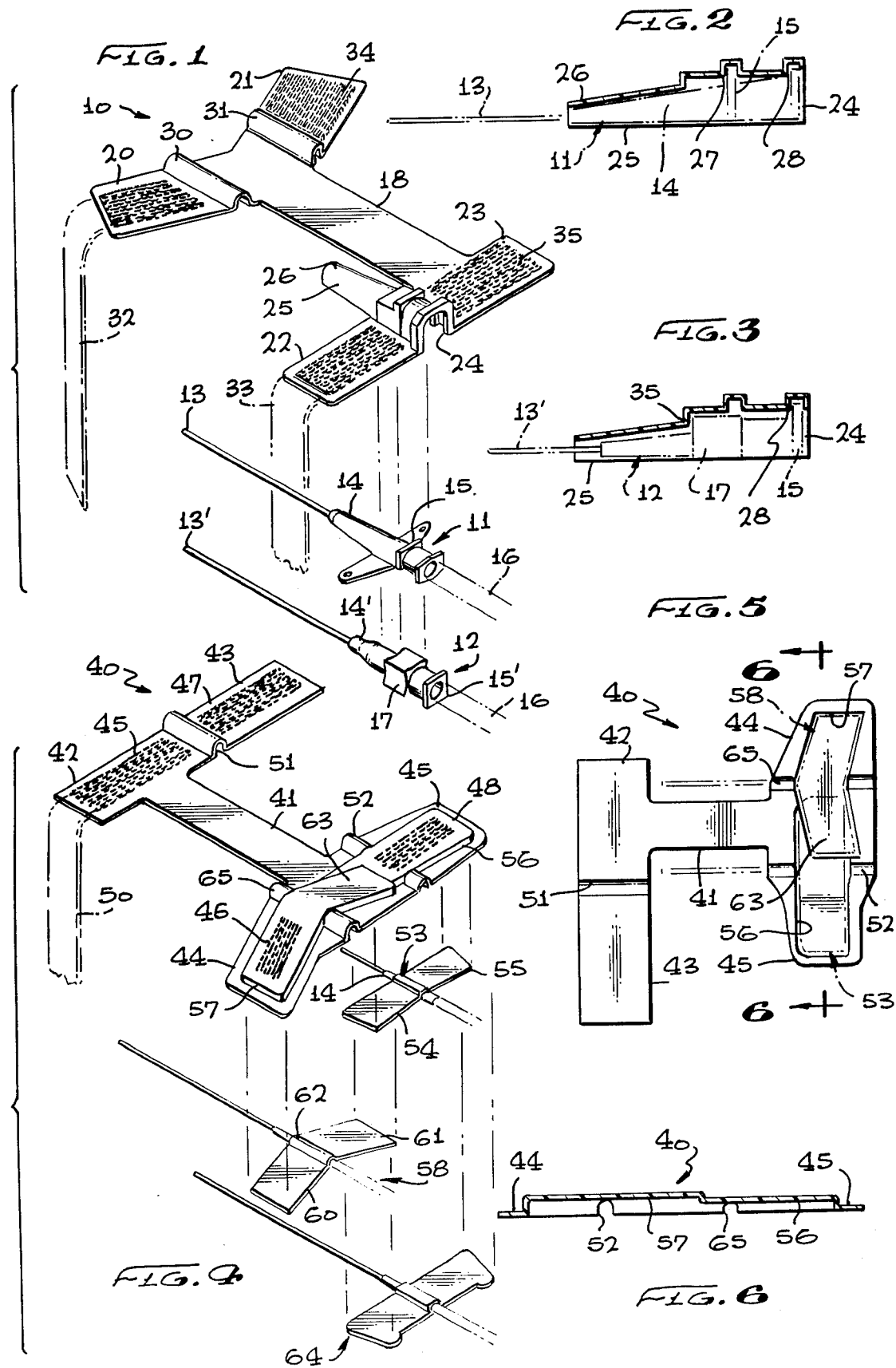

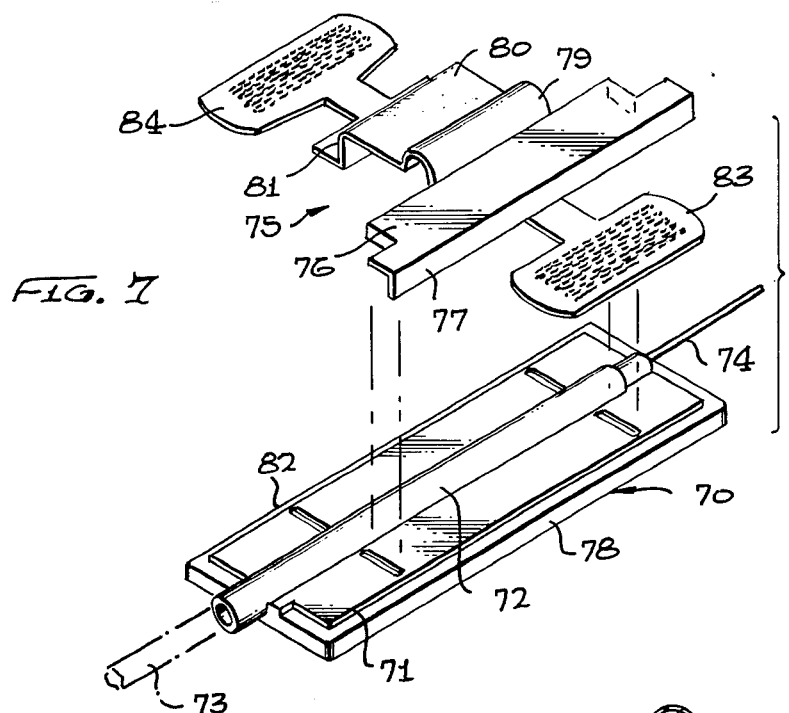
FIG. 7
FIG. 9
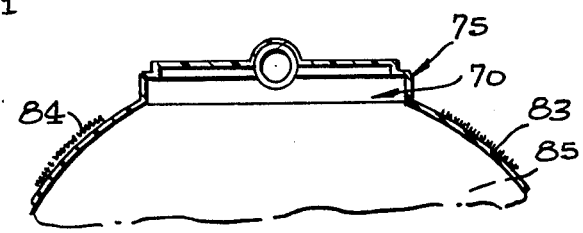
FIG. 8
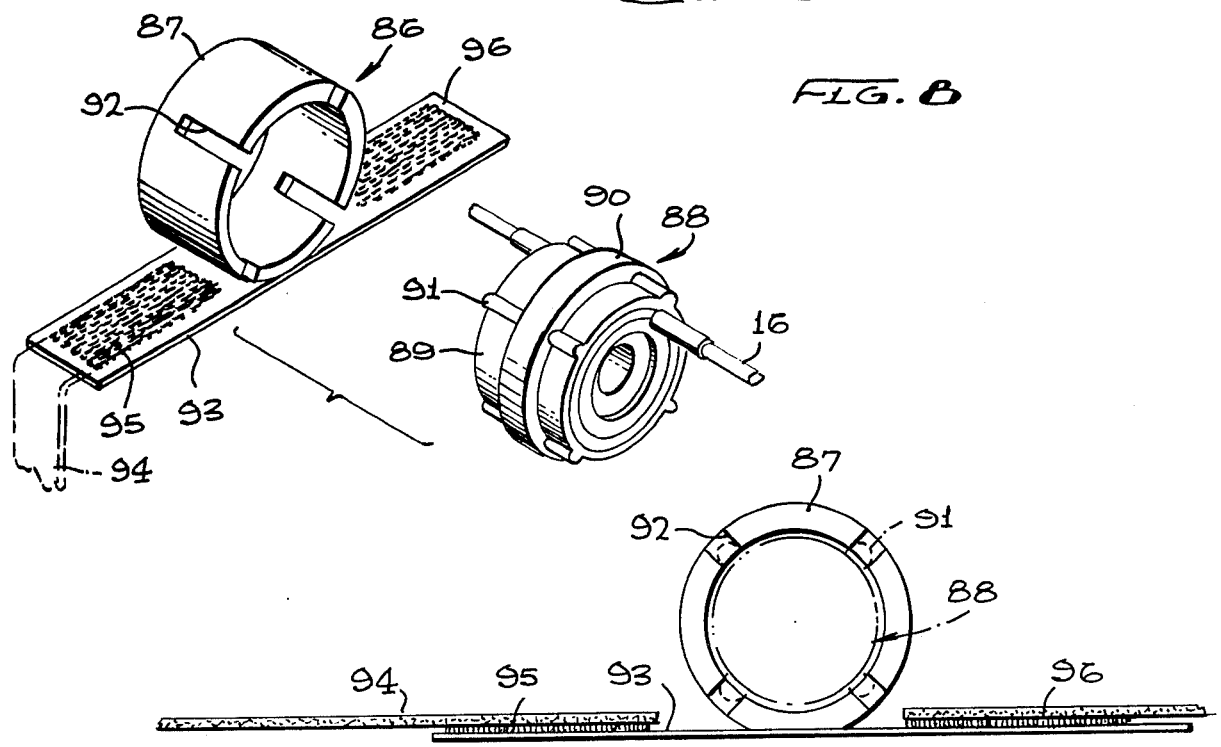
FIG. 10

MEDICAL DEVICE ASSEMBLY HOLDER

BACKGROUND OF THE INVENTION

1. Field of the Invention

The present invention relates to syringe holders or support devices and more particularly to a novel holder for detachably retaining a syringe in position about the limb or body part of a patient undergoing a medical procedure.

2. Brief Description of the Prior Art

In the past, it has been the conventional practice to insert the needle of a syringe into a vein of a patient undergoing medical treatment and the syringe as well as its attendant fluid feeding tubes are retained on the limb by adhesive tape which is wrapped about the syringe, tubing and the limb of the patient. During normal medical procedure, it is routine practice to check fluid flow through the syringe by replacing the tubing periodically since collapse of the tubing is sometimes encountered when the fluid iintroduced to the patient via the syringe has been exhausted. During such a checking procedure, the tubing is removed from the syringe which sometimes causes the syringe needle to be inadvertantly withdrawn from its insertion into the vein of the patient. Obviously, such a procedure is cumbersome and awkward as well as painful and inconvenient to the patient, especially when re-insertion of the syringe needle is required.

Furthermore, when adhesive tape is used, it is the conventional practice to shave hair from the attaching surface prior to adhesion of the tape so that the tape may be readily removed without extreme discomfort to the patient. Such a procedure is additive and presents cosmetic problems, particularly in the instance of women patients.

Therefore, a need has existed to provide a simple and economical means for holding a syringe in position during a medical procedure which may be readily attached to or detached from the patient and that may be disposed with the syringe after use. Such a holder must be easy to place upon the limb of the patient and must be adapted to hold not only the syringe but the tubes feeding fluid to the syringe as well.

SUMMARY OF THE INVENTION

Accordingly, the above problems and difficulties are obviated by the present invention which provides a novel holder for releasably retaining a conventional syringe in place on the body of a person undergoing medical treatment. Preferably, the syringe holder includes a flat base having at least a pair of outwardly extending support members arranged in fixed, parallel spaced apart relationship and outwardly projecting from one side of the flat base. A selected one of the support members is provided with a shaped recess for insertably receiving the syringe and a snap-lock slot is formed in the support member coextensive with the recess for releasably retaining the syringe in place on the support element. Retainer means are operatively carried on the holder base for supporting and retaining the tubing used to introduce fluids to the syringe while hook and pile fastening means are cooperatively disposed on opposite sides of the base for detachably coupling together so that the holder is held on a limb or other body portion of the person undergoing medical treatment.

Therefore, it is among the primary objects of the present invention to provide a novel syringe holder for supporting and retaining a syringe including the tubing feeding the syringe while the syringe needle is insertrd into the limb of a person undergoing medical treatment.

Another object of the present invention is to provide a novel syringe holder which is relatively inexpensive to manufacture so that the item may be considered a disposable unit along with its attendant syringe and needle therefor.

Still another object of the present invention is to provide a novel holder for a medical needle apparatus which is inserted into the limb or body portion of a person during a medical procedure so that the needle need not be removed during inspection or checking procedures necessary to remove the tubing from the needle device.

Still a further object of the present invention is to provide a novel holder for a medical needle which may be readily attached or detached to the arm or limb of a patient so that the needle is held in place and wherein the assembled holder and needle may be discarded as a unit after use.

Yet another object of the present invention resides in the provision of a syringe housing having a shaped recess for receiving or forming fitting with a syringe body of more than one shape.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 1 is an exploded view of the novel needle or syringe holder of the present invention illustrated in a typical medical procedure;

FIGS. 2 and 3 are enlarged longitudinal cross-sectional views of the novel needle or syringe holder of the present invention taken in the direction of arrow 2—2 of FIG. 1 showing fitted retention of two different syringe bodies;

FIG. 4 is an exploded perspective view of another embodiment of the invention adjusted to receive syringes having different body shapes;

FIG. 5 is a top plan view showing the novel needle or syringe holder shown in FIG. 4;

FIG. 6 is a transverse cross-sectional view of the novel needle or syringe holder shown in FIG. 5 as taken in the direction of arrows 6—6 thereof;

FIG. 7 is an exploded perspective view of still another embodiment of the present invention;

FIG. 8 is a cross-sectional view of the holder shown in FIG. 7;

FIG. 9 is a perspective view of yet another embodiment of the invention intended to be used with a rotary fluid metering device; and FIG. 10 is a transverse cross-sectional view of the holder shown in FIG. 9.

DESCRIPTION OF PREFERRED EMBODIMENTS

Referring to FIG. 1, one version of the novel needle or syringe holder incorporating the present invention is illustrated in the general direction of arrow 10 which is illustrated preparatory for mounting on the arm of a patient undergoing a medical procedure. A shaped syringe body of one configuration is indicated by numeral 11 while another configuration is indicated by numeral 12. A needle 13 and 13 prime is carried by each syringe body at its forward end which is inserted through the skin of the patient into an appropriate vein. Each syringe body further includes a coupling element 14 and 14 prime respectively which includes an enlarged semi-encircling flange 15 and 15 prime respectively that is carried about the element 14 and 14 prime. As is the conventional practice, the coupling element 14 or 14 prime is inserted into the rear end of the respective syringe body as illustrated and its opposite end is attached to one end of a fluid carrying tube indicated by the numeral 16. The syringes 11 and 12, needles 13 and 13 prime, coupling elements 14 and 14 prime, and tubing 16 are conventional and do not, in themselves, form a part of the present invention. It is to be particularly noted that the body portions or coupling elements of the syringes are of different shapes such that the coupling element 14 of syringe 11 is cylindrical in cross section terminating in the flange 15 while the coupling element 14 prime in the embodiment 12 includes a block or square shape, in cross section, 17 which is followed by a cylindrical portion terminating in the flange 15 prime. Therefore, to be effective, the needle or syringe holder 10 must be able to receive and hold either of the specially shaped and configured syringes 11 or 12.

The needle or syringe holder 10 of the present invention includes an elongated flat base 18 having a pair of outwardly extending retainers or support members that are arranged in fixed spaced apart relationship on opposite ends of the base 18. For example, support members 20 and 21 outwardly project from one end of the base 18 while support members 22 and 23 outwardly project from the opposite end. Either syringe 11 or 12 is captured within a recess 24 formed by a structure 25 integrally formed in the support member 22 so that the syringe is forcibly urged against the skin of the patient's limb and, therefore, held in place. The structure 25 includes an elongated portion adapted to receive the connecting element 14 or 14 prime of the syringe and the elongated portion is identified by numeral 26. The rear end of the elongated portion 26 terminates in a pair of hollow projections 27 and 28 which are adapted to receive flange 15 associated with syringe 11 or flange 15 prime carried on the end of syringe 12 respectively. The syringe holding or retaining structure 25 is provided with a longitudinal axis which lies substantially parallel to the longitudinal axis of the base 18 and is disposed along one edge thereof in spaced apart relationship.

It is to be particularly noted that the support memebrs 20 and 21 are connected to the one end of base 18 by semicircular portions 30 and 31 which are open through one side or bottom thereof so as to removably engage with the feeding tube 16. In addition to supporting the tube 16, the retaining portions 30 and 31 provide a spring release to accommodate handling of the tube without disturbing the needle 13 or 13 prime. Thereby, the tube 16 including the coupling element 14 or 14 prime may readily be detached from the back end of the syringe 11 or 12 respectively without disturbing the needle from its location. The holder 10 holds the syringe and needle in position permitting the tubing and the coupling elements 14 and 14 prime respectively, to be removed and replaced.

It can be sseen that the holder 10 is mounted or carried on the limb of the patient by a fastening means which includes two sets of strap-like fasteners taking the form of a a hook and pile type. The straps are identified by numerals 32 and 33 having one end of each strap secured to support members 20 and 22 respectively while the opposite end of each strap is joined by a corresponding fasteners 34 and 35.

Referring now to FIG. 2, it can be seen that the structure 25 of the holder 10 holds or retains the syringe 11 in position since the flange 15 carried on the body thereof is captured within the recess of the projection 27. The forward portion of the syringe 11 constituting coupling element 14 is captured beneath the tapered cylindrical portion 26 of the structure 25.

Referring now in detail to FIG. 3, it can be seen that the syringe 12 is captured within the same recess 24 of the structure 25 wherein the square 17 of the syringe is captured by a shoulder 35 of the structure 25 and the flange 15 prime is captured within the recess or hollow of projection 28.

A feature of the present invention includes the provision of a one piece or unitary construction in that the structure 25 is integrally formed with the support elements 22 and 23 and the elongated base 18. Also, the support elements 20 and 21 and the tube retainers 30 and 31 are integrally formed. Therefore, the entire syringe holder may be considered of a sungle unit and may be considered a disposable unit when the need for its use is no longer required. Preferably, the material is pliable so that the tubing 16 may be readily slipped under the retainers 30 and 31 for restraining purposes.

Referring now in detail to FIG. 4, another embodiment 40 of the present invention is illustrated which is similar to the embodiment 10 shown in FIG. 1 in that an elongated body 41 is included having support members 42 and 43 integrally formed on one end and support members 44 and 45 integrally carried on the opposite end. The support members respectively carry the opposite ends for attaching fastener means such as straps capable of attaching to the support elements by conventional hook and pile fastening means. For example, pads of a hook material may be represented by numerals 45, 46, 47 and 48 which are detachably connected with the opposite ends of a strap, such as strap 50 which may engage with the respective pads by a pile fabric. The holder 40 further includes integrally formed tube retaining means taking the form of semicircular portions 51 and 52 which are open ended and receptive to receiving tube 16 as previously described.

The embodimant of FIG. 4 is intended to retain needle syringes known in the trade as "butterflies" in that a syringe body 53 includes outwardly projecting wings or members 54 and 55. The support element 45 is provided with a rectangular structure 56 which includes a recess opening underneath the element so as to receive the syringe body 53 and the outwardly extending wings or elements 54 and 55. The tube 16 passes through the rear of portion 52 while the coupling element 14 of the syringe including the needle 13 passes through the forward end of the portion 52.

The support element 44 is similarly provided with and elongated structure 57 which includes a recess opening from its underside in order to receive another embodiment of a syringe identified by numeral 58 which includes downwardly angled wing-like elements 60 and 61 outwardly projecting from the central body 62 of the syringe. Therefore, it can be seen that by providing a pair of structures 56 and 57 having overlapping portions such as at numeral 63 a variety of different shaped and size syringes may be accommodated. Still another shape of syringe is indicated by numeral 64 which includes outwardly projecting wing-like elements of yet another configuration which would be readily accommodated within the structure 56.

As shown more clearly in FIG. 5, the underside of the holder 40 is illustrated wherein the structure 56 overlaps with the structure 57 at numeral 63 so as to readily accommodate a variety of syringe configurations of the outwardly projecting element type. Also, it is noted that the structure 56 includes a semi-circular portion 65 for conducting the tube 16 and the coupling portion 14 of the syringe therethrough. Furthermore, it can be seen that the portion 51 carried on the support member 43 is in substantial alignment with the retaining duct or portion 52 so that the tubing 16 may also be arranged in alignment therewith depending upon the desired installation of the syringe and its tubing.

FIG. 6 shows a transverse cross-sectional view of the structures 56 and 57 so that the recess opening underneath is clearly identified and visible. Any one of the variety of "butterfly" type syringes may be fitted into the recess of either structure 57 or 56 and, if desired, two syringes of different varieties may be retained by the holder 40 as may be desired for the particular medical procedure.

Referring now in detail to FIG. 7, another embodiment of the present invention is illustrated which is employed for retaining or holding a rigid medical element such as a filter and/or air eliminator which is broadly identified by numeral 70. Such an item is of conventional design and is available from ordinary vending sources. Such a filter or air eliminator includes an elongated member 71 to which is attached a flow line or duct 72 to which tubing 73 and 74 may be attached to its opposite ends. This unit is normally carried on the arm or leg of a patient and is generally taped to the limb for retention. However, by employing the novel holder 40 indicating in the general direction of 75, the need for tape and other lashing are eliminated. The holder 75 includes an elongated structure 76 which includes a recess opening through its bottom for receiving the shaped upper side of a selected side of the rigid filter or eliminator 70. The structure 76 includes a downwardly depending rail 77 that bears against the selected side 78 of the filter or air eliminator 70 while the opposite end of the structure is integrally formed with a semicircular portion 79 adapted to form fit over the duct 72. The opposite side of the portion 79 from its side connected to the structure 76 is provided with an extension 80 which terminates in a downwardly depending shoulder 81 adapted to engage with the side 84 of the filter or eliminator 70 from the side 78. Therefore, it can be seen that the structure 76, portion 79, extension 80 and downwardly depending rails 77 and 81 form fit across the top and down the opposite side of the filter or eliminator 70. Attachment to the rim is made by supporting members or tabs 83 and 84 which are attached to the shoulder 81 and rail 77 respectively. Straps or fasteners of the hook and pile type may be employed for joining the tabs by being wrapped or passed around the limb of the user and fastened in accordance with conventional procedures.

Referring now to FIG. 8, it can be seen that the device or holder 75 is conformal to the shape and corresponds in general to the contour of the size and upper surface of the filter or eliminator 70. The tabs 83 an 84 pass around the limb which is broadly identified by numeral 85. Adhesive tape may also be placed underneath the tabs for direct attachment to the body.

Referring now to FIG. 9, another embodiment of the present invention is shown wherein the holder is indicated in the general direction of arrow 86 and takes the form of a circular ring 87 adapted to receive and hold a metering device such as is conventionally available through commercial sources. The conventional meterin device is illustrated in the general direction of arrow 88 and includes a cylindrical body 89 having a rotary ring 90 disposed between a plurality of spaced apart ribs, such as rib 91. Tubing 16 passes through a body 89 of the device and the device is slipped into the ring 87 by inserting the plurality of spaced apart ribs into respective open ended slots, such as slot 92 in the ring 87. As shown in FIG. 10, the ring 87 is attached to an elongated support member 93 which includes a fastening strap 94 adapted to releasably engage with the opposite ends of the support member 93 via a hook and pile fastening system. For example, numeral 95 may be of a hook and pile connection between one end of the strap and the support member 93 while numeral 96 shows a similar hook and pile connection with the opposite end of the strap 94 after the strap has been wound about the limb of the wearer. In this fashion, not only is the device 88 supported but the tubing 16 as well. In the event it is necessary to meter or change the regulation of the fluid passing through the tubing, the device 88 may be readily adjusted in place on the ring.

Therefore, in view of the foregoing, it can be seen that the various and variety of syringe holders incorporating the present invention provides a novel way for supporting a variety of syringes or other medical devices and a feeding tube in a convenient and economical manner on the body of a patient undergoing a medication or medical procedure. In actual use, the needle 13 is inserted through the skin of the patient and the syringe such as syringe 11 is held while the recess in the structure 25 is registered with the syringe and placed thereover. At this time, the straps of the fastening means may be employed for encircling the wrist of the arm or other limb of the user and fastened so that the syringe and needle are retained in position. Next, the coupling element 14 can readily be inserted into the syringe 11 while the tubing 16 is clipped under the retaining portions respectively. The support members protect the user from inflammation or other discomfort caused by tape or the like and no preparation is required on the skin of the user such as shaving, etc. In order to change the tubing 16, the coupling element 14 may readily be removed from the back side of the syringe 11 while the syringe and needle 13 are still implanted in the skin of the patient. The holder stabilizes the syringe and by gentle manipulation, the attendant can hold the syringe and pull the coupling element 14 therefrom. When the injection is no longer required, the needle, syringe, tubing and the holder may readily be discarded as a single unit.

Although an actual procedure has been described in connection with the embodiment shown in FIGS. 1–3, it is to understood that a similar procedure is also employed in actual use for the embodiment shown in FIGS. 4–6 inclusive, FIGS. 7 and 8 and FIGS. 9 and 10 respectively.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. In a unitary one-piece integral medical device holder for use in combination with a specially shaped medical device assembly comprising the combination of:

an elongated base;

at least a pair of support members outwardly extending from each end of and integral with said base in fixed, parallel spaced apart relationship;

means integrally carried on a selected one of said support members adjacent to and laterally disposed with respect to said base for releasably holding said medical device assembly thereon;

means carried on said support members for detachably connecting said base to a body portion of a user;

tubing retainers integrally carried at a junction between said support members and said base for removably connecting with said medical device assembly;

said releasable holding means being a shaped structure having an open recess conforming to the configuration of said medical device assembly;

snap-lock means integral with said structure and cooperatively disposed between said structure and said medical device assembly for detachably connecting said medical device assembly to said structure so as to be laterally of and adjacent to said base;

said detachable connection means include a pair of straps and hook and pile fastener arrangements carried on opposite sides of said support members and cooperating to be releasably coupled together; and said shaped structure provided in said selected one of said support members is provided with a shaped recess therein for insertably receiving a portion of said medical device assembly having a conformal shape therewith.

* * * * *